United States Patent [19]

Allan et al.

[11] Patent Number: 5,496,396
[45] Date of Patent: Mar. 5, 1996

[54] GAS FILTER

[75] Inventors: Andrew M. Allan, Blairgowrie; Akis Katsakoglou, Arbroath, both of United Kingdom

[73] Assignee: W. L. Gore & Associates (UK) Ltd., London, United Kingdom

[21] Appl. No.: 284,486

[22] PCT Filed: Feb. 4, 1993

[86] PCT No.: PCT/GB93/00232

§ 371 Date: Sep. 16, 1994

§ 102(e) Date: Sep. 16, 1994

[87] PCT Pub. No.: WO93/14722

PCT Pub. Date: Aug. 5, 1993

[30] Foreign Application Priority Data

Feb. 4, 1992 [GB] United Kingdom ............... 9202360

[51] Int. Cl.⁶ ............... B01D 29/05; B01D 53/04
[52] U.S. Cl. ............... 96/135; 96/147; 96/153; 55/385.4; 55/514; 55/DIG. 5
[58] Field of Search ............... 55/385.4, 514, 55/524, DIG. 5; 95/46, 136; 96/6, 135, 147, 153, 154; 604/333

[56] References Cited

U.S. PATENT DOCUMENTS

| | | | |
|---|---|---|---|
| 3,416,293 | 12/1968 | Alexander | 95/136 |
| 3,575,170 | 4/1971 | Clark | 96/6 |
| 3,953,566 | 4/1976 | Gore | 264/288 |
| 4,208,194 | 6/1980 | Nelson | 55/385.4 X |
| 4,268,286 | 5/1981 | Steer et al. | 55/385.4 X |
| 4,274,848 | 6/1981 | LaGro | 96/6 |
| 4,449,970 | 5/1984 | Bevan et al. | 55/385.4 X |
| 4,451,258 | 5/1984 | Jensen | 55/385.4 X |
| 4,460,392 | 7/1984 | Poulsen et al. | 96/153 X |
| 4,479,818 | 10/1984 | Briggs et al. | 55/385.4 |
| 4,512,771 | 4/1985 | Norton | 55/385.4 X |
| 4,516,974 | 5/1985 | Davis | 55/385.4 X |
| 4,614,310 | 9/1986 | Tloczynski et al. | 241/259.2 |
| 4,668,258 | 5/1987 | Steer | 55/524 X |
| 4,841,623 | 6/1989 | Rine | 29/525.1 |
| 4,875,899 | 10/1989 | Holtermann | 55/385.4 X |
| 4,940,461 | 7/1990 | Steer | 55/385.4 X |
| 4,957,518 | 9/1990 | Brassell | 55/385.4 X |
| 5,063,196 | 11/1991 | Doughty et al. | 95/136 X |
| 5,074,851 | 12/1991 | Plass et al. | 96/153 X |
| 5,250,042 | 10/1993 | Torgalkar et al. | 604/333 |
| 5,370,638 | 12/1994 | Keyes | 55/385.4 X |
| 5,401,264 | 3/1995 | Leise, Jr. | 604/333 |

FOREIGN PATENT DOCUMENTS

| | | | |
|---|---|---|---|
| 0443728 | 8/1981 | European Pat. Off. | |
| 0358316 | 3/1990 | European Pat. Off. | |
| 1399213 | 6/1972 | United Kingdom | |
| 1550960 | 8/1979 | United Kingdom | 96/135 |
| 2059797 | 4/1981 | United Kingdom | |
| 2139501 | 11/1984 | United Kingdom | |
| 2242431 | 3/1991 | United Kingdom | |

OTHER PUBLICATIONS

Patent Abstracts of Japan vol. 8, No. 255 (C–253) (1984)—JP, A, 59 133 386 (Asahi Glass).

*Primary Examiner*—Robert Spitzer
*Attorney, Agent, or Firm*—Gary A. Samuels

[57] ABSTRACT

An ostomy filter for colostomy and ileostomy bags is gas-permeable to allow venting, and liquid-impermeable to prevent leakage. It includes a hydrogen sulphide adsorbent to remove smells. The filter comprises 9 to 50% by weight of particles of unsintered granular polytetrafluoroethylene (PTFE), 30 to 82% by weight of particles of comminuted sintered expanded porous PTFE, and 9 to 30% by weight of particulate water-insoluble $H_2S$ adsorbent. The particles are fused together by baking at elevated temperature to form a gas-permeable liquid-impermeable network. The comminuted sintered expanded porous PTFE is preferably formed by comminuting uniaxially expanded PTFE fibre.

16 Claims, No Drawings

GAS FILTER

FIELD OF THE INVENTION

The present invention relates to an ostomy filter which allows gas to be vented from colostomy and ileostomy bags, whilst at the same time filtering out any unpleasant smell, particularly hydrogen sulphide.

BACKGROUND

After undergoing a colostomy or ileostomy operation, the patient is fitted with a disposable bag which receives the waste contents of the intestine. The bag is disposable and is emptied or replaced at regular intervals. To avoid the bag becoming over inflated by virtue of gas generated by the fermenting food matter, it is desirable to provide a vent. However, the vent requires to be filtered in order to prevent embarrassing smells being released.

It is currently conventional practise in colostomy bags to provide an activated charcoal filter in the form of a disc as the vent. For example the disc may have a diameter of 23.5 mm and be formed of activated carbon contained within a foamed polyurethane material, having polypropylene net facings on either or both sides to improve its strength and other mechanical properties. However, this conventional filter material has the significant disadvantage of being liquid-permeable, so that if the patient sits or lies down there is a significant danger of leakage of liquid through the filter onto the patient's skin or his clothing. This is particularly the case with ileostomy bags, where the bag is connected into the early part of the intestine where the food matter is largely undigested and still fermenting, and has a high liquid content. In fact conventional ileostomy bags are not provided with vents, and the filters used for colostomy bags would be quickly saturated with liquid if used for ileostomy.

A porous polytetrafluoroethylene structure containing active carbon is disclosed in our British patent application GB2242431. However, the material disclosed is insufficiently gas permeable.

It is an object of the present invention to provide an ostomy filter which mitigates these problems.

Patent specification GB 1399213 discloses a gas-permeable liquid impermeable membrane which includes finely divided high surface area carbon for the production of hydrogen peroxide.

SUMMARY OF THE INVENTION

The invention provides a gas permeable and liquid impermeable ostomy filter for colostomy and ileostomy bags which comprises a mixture of;

(i) particles of unsintered granular-type polytetrafluoroethylene (PTFE);

(ii) particles of comminuted sintered expanded porous polytetrafluoroethylene (PTFE); and (iii) a particulate water-insoluble hydrogen sulphide adsorbent; the particles being fused together such as to form a gas permeable liquid impermeable network of interconnected particles.

PREFERRED EMBODIMENTS

The permeable nature of the polytetrafluoroethylene (PTFE) structure results from the particulate nature of the PTFE used to form it. The baking conditions are chosen such that the PTFE particles become partially fused or sintered into an integral permeable network during baking.

A feature of the present invention is that granular type PTFE is employed as a component. As is well known, PTFE can exist in two quite different forms viz; the granular form produced by precipitation polymerisation techniques, and the powdered form produced by dispersion polymerisation processes (i.e. fine-powder PTFE). These two types of PTFE have quite different properties and have to be considered separately.

Unsintered granular PTFE generally has a crystallinity in excess of 95% as determined by differential scanning calorimetry or by infra-red techniques. The degree of crystallinity is reduced by sintering (i.e. baking), and the finished structure of the present invention will typically have a crystallinity of less than 95%, often less than 80%. An unsintered granular PTFE is available from DuPont as Grade 7A.

The average particle size of the granular-type PTFE is usually in the range 1–500, particularly 1–200, especially 1–100 microns. Depending on the desired porosity of the structure, the particles may have substantially the same particle size, or a range of varying particle sizes may be included which pack to influence the porosity of the structure. The granular PTFE may be milled or unmilled.

The comminuted porous expanded polytetrafluoroethylene (PTFE) material comprises irregularly shaped particles of porous expanded PTFE. The starting material from which the comminuted expanded PTFE particles are produced may be any form of sintered porous expanded PTFE, such as film, sheet, rod, fibre or tube. It is preferably produced by comminuting (e.g. by chopping or grinding) expanded porous PTFE material (produced as described in U.S. Pat. No. 3,953,566) to a particle size of 5 to 200 microns, particularly 40–100 microns. Generally speaking, the lower limit of particle size is 5 microns, preferably 20 microns and more preferably 40 microns; whilst the upper limit is 500 microns, preferably 200 microns and more preferably 100 microns. The structure of porous expanded PTFE is well known, being characterized by nodes interconnected by fibrils as described in U.S. Pat. No. 3,953,566 to form a waterproof, but water vapor-permeable porous material. The expanded PTFE is sintered to give dimensional stability, and to mitigate shrinkage during baking of the mixture to form the filter material. The particles of sintered porous PTFE may be produced by shredding or chopping sintered porous expanded PTFE to reduce it to small pieces, and then grinding these porous expanded PTFE pieces in water between closely spaced grinding surfaces to obtain sheared and ground particles of porous expanded PTFE, separating the sheared and ground particles from the water and drying the separated particles. Any suitable apparatus for grinding or comminuting tough polymeric or elastomeric materials may be used for producing the porous expanded PTFE particles, such as the apparatus disclosed in U.S. Pat. Nos. 4,614,310 and 4,841,623.

In order to deodorise the gas vented from the ostomy bag, hydrogen sulphide is filtered out by adsorption. The hydrogen sulphide adsorbent preferably includes a high surface area support material impregnated with a water-insoluble $H_2S$-adsorbent substance. The support material may be any suitable material known in the art, such as activated carbon, diatomaceous earth etc. Activated carbon is commercially available and is formed, for example, by heating carbon with steam to 800°–900° C. In order to avoid removal or deactivation by water, the $H_2S$-adsorbent is water-insoluble, and typically comprises a water-insoluble copper oxide.

A preferred material is activated carbon impregnated with copper oxide. This may be produced by soaking the activated carbon in cupric nitrate solution to produce cupric nitrate, and then drying and igniting to generate black copper oxide attached to the activated carbon. The copper oxide is insoluble in water or ethanol. Hydrogen sulphide is adsorbed by reaction to produce copper sulphide.

In order to provide good $H_2S$ adsorption, the filter preferably comprises 10 to 30% by weight of impregnated high surface area adsorptive material. Typically, the $H_2S$-adsorbent constitutes 2 to 10% of the weight of the support material.

Particularly preferred embodiments of the invention comprise the components (i)–(iii) as defined above in the following weight percentages;
 (i) 9–50%, preferably 10–40% (or 30–50%);
 (ii) 30–82%, preferably 40–80% (or 30–50%); and
 (iii) 9–30%, preferably 10–20% (or 10–30%).

The filter material is generally formed by applying to a substrate a suspension comprising the mixture of PTFE particles and impregnated support material, allowing to dry and baking at a temperature usually in the range 335° to 350° C. for 0.5 to 3 hours. However, the conditions may be varied when the process is conducted as a continuous operation, when reduced heating times of 1 to 30 mins may be used. The thickness may be created in a single step or may be built up by applying a number of layers and allowing each to dry between applications, prior to baking the layered composite. Generally, the process is conducted at substantially atmospheric pressure. Spraying ensures that no air pockets are left between the substrate and the coating. However, other known application techniques, such as a doctor blade can be used. The suspension is usually an aqueous suspension comprising appropriate surfactants, thickening agents and/or suspending agents. The temperature may be progressively raised over a few hours e.g. 1 to 10 hours in order to remove such additives, prior to baking.

The structure of the present invention generally has a specific gravity of 0.5 to 1.0, usually 0.6 to 0.9. The specific gravity tends to go down as the proportion of comminuted PTFE increases. In comparison, solid PTFE typically has a specific gravity of 2.16. It is important to get good gas permeability commensurate with acceptable physical strength.

The gas permeable PTFE filter is generally hydrophobic in nature and typically has a water entry pressure (measured as described in GB 2242431) in excess of 1.5, preferably 2.0 lbs per square inch. It is therefore liquid impermeable under normal conditions of usage.

The thickness of the filter will vary depending on the desired gas permeability and degree of adsorption, but is usually in the region 0.8 to 6 mm, preferably 1 to 5 mm, and especially 1.5 to 2.5 mm.

The filter preferably allows a gas flow rate in excess of 1 liter per hour, preferably at least 5 liters, more preferably at least 10 liters per hour. Typical gas flow rates from a patient are approximately 2.5 liters per day, though peak flow rates during a day may exceed this. The filter is preferably capable of maintaining a level of $H_2S$ in the filtered gas below one part per million for at least 20, preferably 40 minutes. In normal use on a patient this means that the filter would require changing every day or two. Principal gas flows occur after each meal as the food is digested. The filter is usually in the shape of a disc and may be arranged for flow of gas in a direction perpendicular to the plane of the disc. Alternatively for a longer flow path, it may be arranged to flow radially from a central entry point to the periphery of the disc (or vice versa). This may be achieved by skinning the surface of the filter disc during production and providing a central pinhole entry, or by masking the corresponding areas.

The ostomy filter of the present invention has a high water entry pressure which makes the filter impervious to liquid water under normal conditions of operation, whilst having good gas permeability and $H_2S$ removal capacity. By including impregnants for different gases in the support material, the filter can be adapted to remove gases other than hydrogen sulphide.

The invention also relates to an ostomy bag including the filter, either as a removable replaceable filter element or integral with the bag (e.g. heat welded to the bag).

DETAILED DESCRIPTION OF PREFERRED EMBODIMENTS

Embodiments of the invention will now be described by way of example only.

PREPARATION OF COMMINUTED EXPANDED POROUS POLYTETRAFLUOROETHYLENE PARTICLES.

Comminuted expanded porous PTFE was produced from sintered porous expanded PTFE material obtained from W. L. Gore & Associates, Inc. in sheet, rod, fibre or tube form. The porous expanded PTFE material was cut into pieces of about 6 mm (quarter inch) largest dimension in a rotary cutting mill. The cut material was mixed with water to form a slurry, and the slurry fed between closely spaced grinding surfaces of a grinding mill, such as that disclosed in U.S. Pat. No. 4,841,623, to crush and shear the pieces of porous expanded PTFE into particles. The ground slurry is then filtered or centrifuged to separate the porous expanded PTFE particles from the water, and the separated finely ground particles were oven dried at from 125° C.–150° C.

The product was a comminuted porous expanded PTFE material comprising finely ground particles of irregular shape.

The comminuted particles preferably will have a mean particle size between 20 and 500 microns, preferably between 40 and 200 microns. Particle size was determined as follows: using a magnetic stirrer and ultrasonic agitation, 2.5 grams of milled PTFE powder were dispersed in 60 ml isopropyl alcohol. (Ultrasonic Probe Model W-385, manufactured by Heat Systems-Ultrasonics, Inc.). Aliquots of 4–6 ml of the dispersed particles were added to approximately 250 ml of circulating isopropyl alcohol in a Leeds & Northup Microtrac FRA Particle Size Analyzer of analysis. Each analysis consisted of three 30-second runs at a sample circulation rate of 2 liters/minute during which light scattering by the dispersed particles is automatically measured and the particle size distribution automatically calculated from the measurements.

The particles will preferably have an average surface area of between 1 and 3 $m^2/gm$, as determined by specific surface area measured by a Leeds and Northrup surface area analyzer. The surface area analyzer uses the BET (1) method to calculate surface area. In this sample analysis, the desorption isotherm of a single point analysis was used to calculate the surface area.

EXAMPLE 1

The general procedure outlined in British Patent Publication GB 2242431A was followed. Teflon grade 7A resin (DuPont Speciality Polymers Division, Wilmington, U.S.A., average specific gravity 2.16 and particle size 35 microns)

was mixed with the comminuted PTFE (particle size 50 to 100 microns), and activated carbon grade 209M (Sutcliffe Speakman) in the following percentages by weight:

Solids:
- 40% PTFE grade 7A
- 40% comminuted PTFE
- 20% activated carbon 209M

The solids were then blended in a Waring blender for 5 mins with liquid of the following composition by weight, in a ratio of 1 kg solids to 2 l of liquid, to produce a suspension.

Liquid:
- 43% water
- 43% carboxymethyl cellulose
- 6% Zonyl FSN100 surfactant
- 8% Pluronic L121 surfactant Pluronics are a class of polyethylenepolypropylene glycol non-ionic surfactants.

The suspension was then sprayed as a coating onto a metal tray (as described in GB 2242431A) as a single layer. The thickness of the sprayed layer was about 20% greater than the desired thickness in the finished sample, to allow for shrinkage during baking. The coating was then dried in an oven at 115° C. for 30 mins. The temperature was raised to 280° C; then progressively to 333°–348° C. and baked at that temperature for 60 mins.

The specific gravity of the baked coating was 0.78. The water entry pressure was approximately 2 lbs per square inch.

EXAMPLE 2

Samples 1,2 and 3 as produced in Example 1 of varying thickness were cut into discs 23 mm in diameter (4.16 cm$^2$) and tested for gas deodorisation. The test gas comprised 80% nitrogen, 20% methane and 25 ppm H$_2$S, and the flow rate was 0.5 l/min. The test apparatus comprised a sample holder, a test gas inlet, an H$_2$S detector and read-out unit.

During the test the gas is allowed to flow to the centre of the filter sample, which is clamped in position in the holder. The gas flow through the sample may be axial or radial (for an increased path). The H$_2$S detector attached to the other side of the sample monitors the efficiency of the filter in removing the hydrogen sulphide. Once this efficiency begins to fall below 100% the detector reading is noted against time. The results are expressed as the time the electrochemical detector remains at zero (and moves to 0.1 ppm) as well as the time taken to reach 1.0 ppm.

The results are shown in Table 1.

TABLE 1

| Sample | Thickness mm | Gas* deodorisation liters | Time to detect [H$_2$S] 1.0 ppm (minutes) | Gas permeability cc/minute** |
| --- | --- | --- | --- | --- |
| 1 | 2.7 | 9 | 18 | 125.0 |
| 2 | 3.3 | 15 | 30 | 30.0 |
| 3 | 4.0 | 52.5 | 105 | 25.0 |

*target value = 9
**pressure of 4 cm waterhead

EXAMPLE 3

The general procedure of Example 1 was repeated with two further compositions as follows:

TABLE 2

| Sample | 4 | 5 |
| --- | --- | --- |
| PTFE grade 7A | 10% | 20% |
| Comminuted PTFE | 80% | 60% |
| Activated carbon 209M | 10% | 20% |
| Gas permeability cc/min/cm$^2$ | 4000 | 1000 |

The comminuted PTFE was formed from Rastex (trademark) fibre expanded at 80:1 and of particle size 50 to 100 microns.

The drying regime employed was as follows. The wet sprayed coating was oven dried at 90° C. overnight. The temperature was then raised to 115° C. Then the temperature was raised progressively from 115° C. to 340° C. over 7 hours. Finally, the coating was baked at 340° C. for 30 mins.

The specific gravity was about 0.6–0.8 g/cc.

The coating was cut into discs about 23 mm diameter and 2 mm thick, and the gas permeability measured using a Gurley Densometer according to standard protocol. The Gurley number is defined as the time in seconds for 100 cc of air to pass through one square inch of filter at 4.88 inches of water pressure differential. The Gurley number is then converted into a gas flow rate in cc/min/cm$^2$. The gas permeabilities are given in Table 2.

We claim:

1. A gas permeable and liquid impermeable hydrogen sulfide filter which comprises a mixture of:
   (I) particles of unsintered granular polytetrafluoroethylene (PTFE);
   (ii) particles of comminuted sintered expanded porous polytetrafluoroethylene (PTFE); and
   (iii) a particulate water-insoluble hydrogen sulphide adsorbent; the particles defined in (I) and (ii) above being fused together such as to form a gas permeable liquid-impermeable network of interconnected particles.

2. A filter according to claim 1 which comprises:
   9 to 50% by weight of component (I) of claim 1;
   30 to 82% by weight of component (ii) of claim 1; and
   9 to 30% by weight of component (iii) of claim 1.

3. A filter according to claim 1 which comprises:
   10% to 40% by weight of component (i) of claim 1;
   40 to 80% by weight of component (ii) of claim 1; and
   10 to 20% by weight of component (iii) of claim 1.

4. A filter according to claim 1 which comprises:
   30 to 50% by weight of component (I) of claim 1;
   30 to 50% by weight of component (ii) of claim 1; and
   10 to 30% by weight of component (iii) of claim 1.

5. A filter according to claim 1 wherein the particles of comminuted porous PTFE have a particle size in the range 40 to 200 microns.

6. A filter according to claim 1 wherein the expanded porous PTFE, from which said comminuted PTFE particles are derived, is material which has been uniaxially expanded to form fibre prior to comminution.

7. A filter according to claim 1 wherein the particles of component (ii) are derived from expanded porous PTFE that has been biaxially expanded to form sheet prior to comminution.

8. A filter according to claim 1 wherein the hydrogen sulphide adsorbent is activated carbon impregnated with copper oxide.

9. A filter according to claim 1 having a specific gravity of 0.5 to 1.0 g/cc.

10. A filter according to claim 1 in the form of a disc of thickness 1.0 to 5.0 mm.

11. A filter according to claim 1 having a gas permeability of at least 500 cc/min/cm$^2$.

12. A gas permeable and liquid-impermeable filter which comprises a mixture of:
- (I) particles of unsintered granular polytetrafluoroethylene (PTFE);
- (ii) particles of comminuted sintered expanded porous polytetrafluoroethylene (PTFE); and
- (iii) a particulate water-insoluble adsorbent comprising activated carbon impregnated with copper oxide;

the particles defined in (I) and (ii) above being fused together such as to form a gas permeable liquid-impermeable network of interconnected particles.

13. A gas-permeable liquid-impermeable material which comprises a mixture of the following components:
- (I) particles of unsintered granular polytetrafluoroethylene; and
- (ii) particles of comminuted sintered expanded porous polytetrafluoroethylene;

the particles defined in (I) and (ii) above being fused together such as to form a gas permeable liquid-impermeable network of interconnected particles.

14. A process for the production of a gas permeable and liquid-impermeable hydrogen sulphide filter material which comprises:
- (A) forming a mixture in liquid suspension of:
  - (i) particles of unsintered granular polytetrafluoroethylene (PTFE);
  - (ii) particles of comminuted sintered expanded porous polytetrafluoroethylene (PTFE); and
  - (iii) a particulate water-insoluble hydrogen sulphide adsorbent;
- (B) applying the liquid suspension to a substrate and allowing to dry; and
- (C) baking so as to fuse the particles defined in (i) and (ii) above together such as to form a gas permeable liquid-impermeable network of interconnected particles.

15. A process according to claim 14 wherein the temperature of the dried suspension is gradually raised to baking temperature over 1 to 10 hours.

16. A process according to claim 14 or 15 wherein baking occurs at 335° to 350° C. for 0.5 to 3 hours.

* * * * *